United States Patent [19]

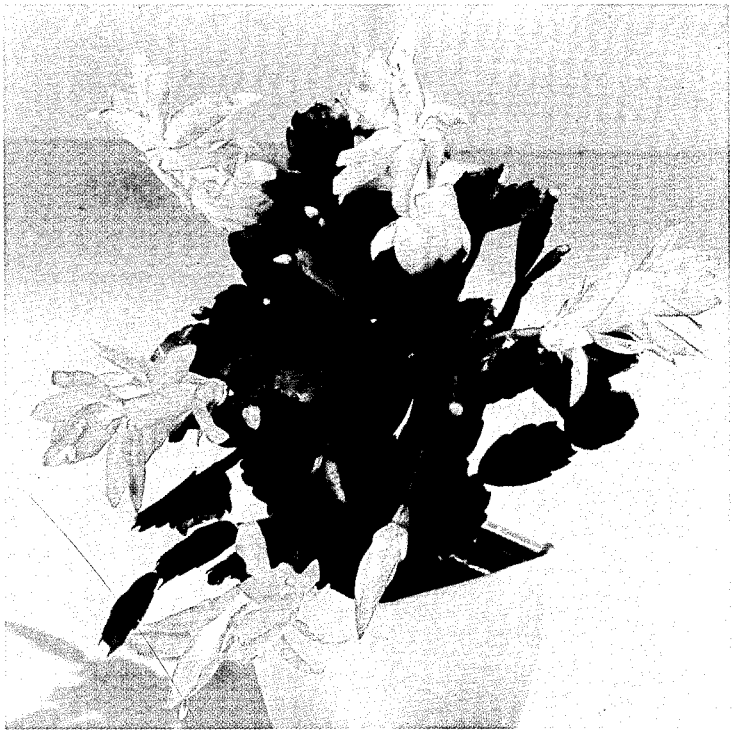
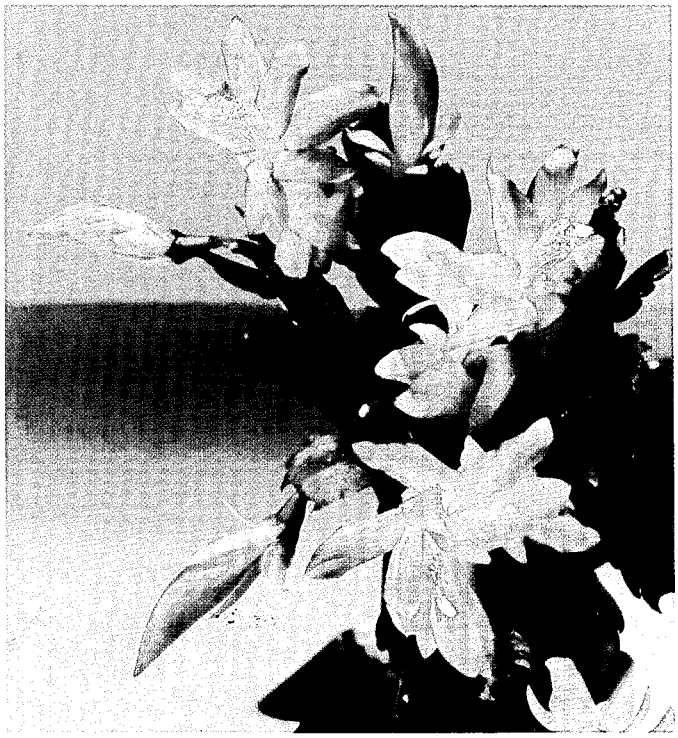

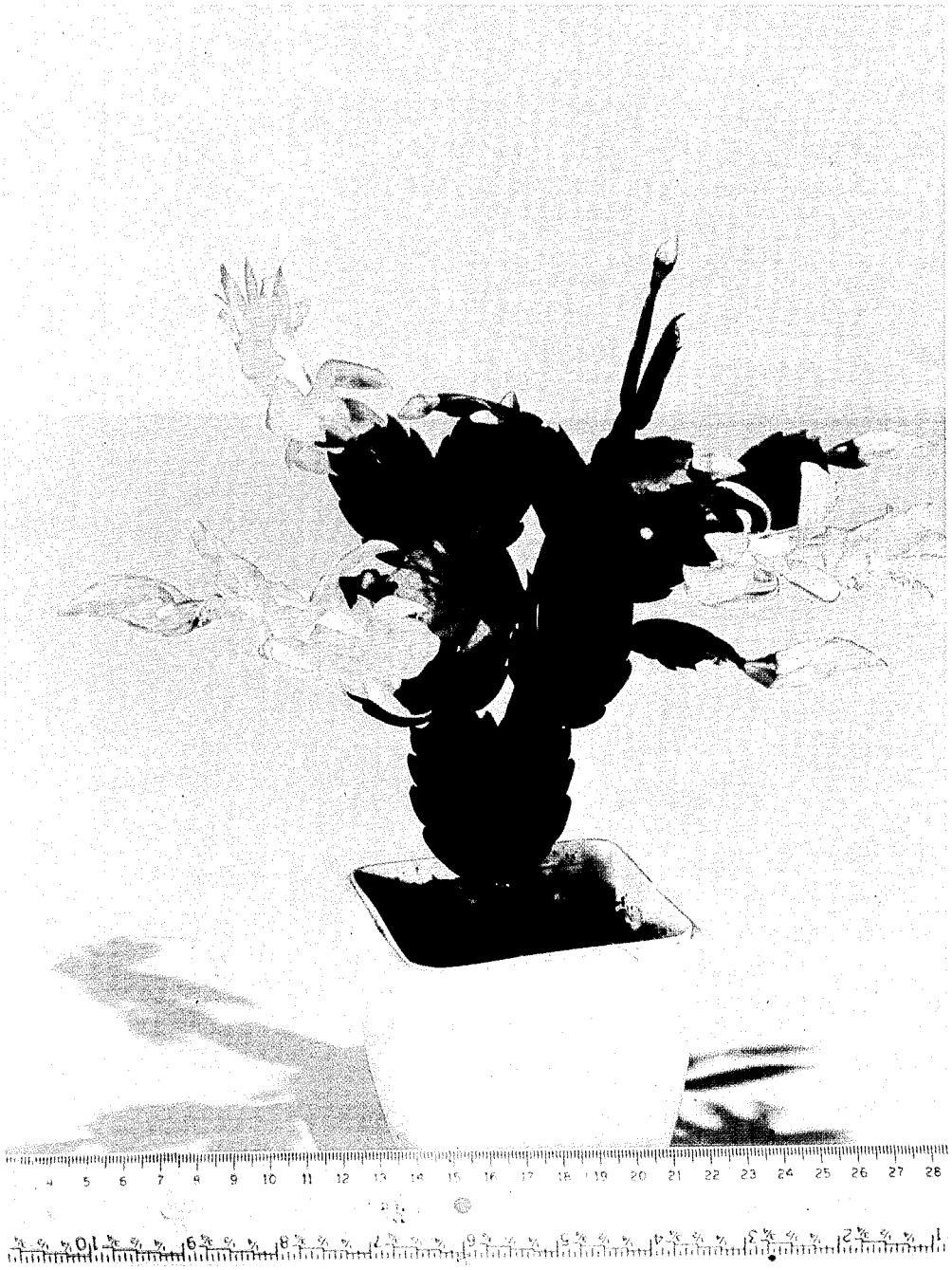

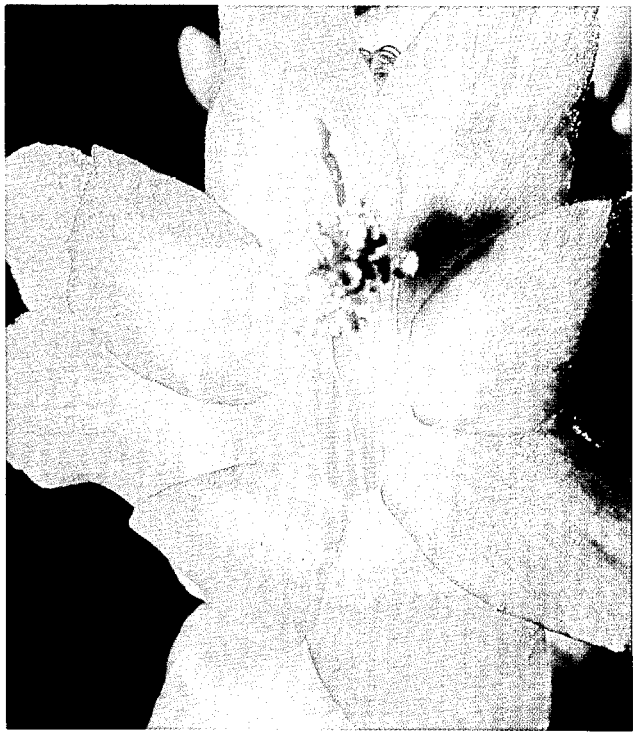
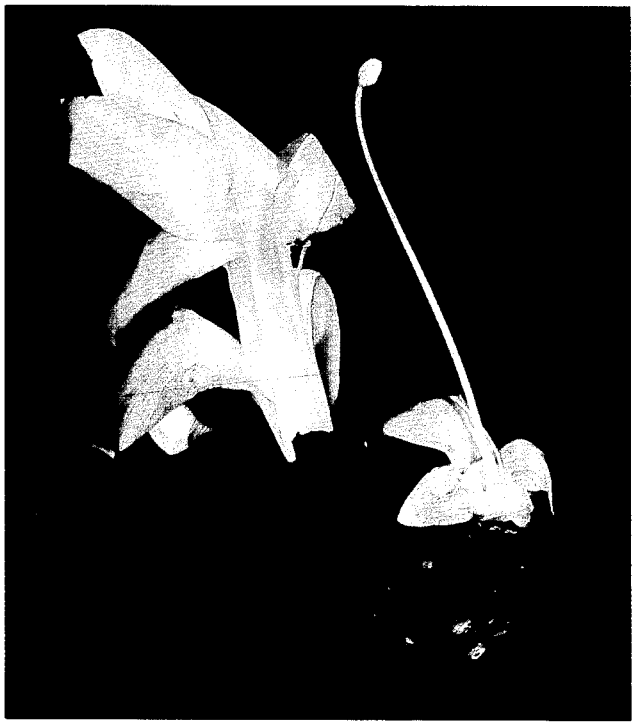

Cobia et al.

[11] Plant 4,196

[45] Jan. 24, 1978

[54] CACTACEAE PLANT

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,336

[22] Filed: Jan. 18, 1977

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct hybrid plant variety of the Cactaceae family is related to the *Zygocactus truncatus* 'Kris Kringle' and *Zygocactus truncatus* 'Lavender Doll' varieties and is principally distinguished by a growth habit which combines characteristics that include a natural tendency to branch without inducement by pruning during the growth period, a fast growth rate with resistances to nutrient deficiencies and fungus type diseases that are comparable to those of the 'Kris Kringle' and 'Lavender Doll' varieties, a resistance to flower bud abscission that is comparable to those of the 'Kris Kringle' and 'Lavender Doll' varieties and a flower that blooms earlier than that of the 'Lavender Doll' variety and has a bloom life of from about 6 to about 9 days, a pistil with a style that is translucent white at its proximal end and in color at its distal end is dominated by purplish red and/or reddish purple hues and with a stigma which is translucent white, and tepals which have marginal blade areas that in color are dominated by purplish red and/or reddish purple hues and which include a sepaloid series of free tepals with inner whorl members having basal areas that in color are dominated by a purplish pink hue, a perianth tube forming series of basally united tepals that form a translucent white vestigal carina at the throat of the tube, and a series of tube laminating tepals which usually number from 5 to 7 in the bloom.

1 Drawing Figure

The invention relates to a new and distinct plant variety of the Cactaceae family and which has been named the *Zygocactus truncatus* 'Christmas Charm' by the inventor.

Certain plant varieties of the Cactaceae family are well known in the foliage plant market and among those are those of the *truncatus* species of the Zygocactus genus. These varieties tend to bloom in the months of November and December in the Northern Hemisphere and hence they appear in the retail market area primarily during the Thanksgiving and Christmas seasons and wherein they are commonly referred to as a "Christmas Cactus".

The *Zygocactus truncatus* 'Kris Kringle' forms the subject matter of U.S. Plant Pat. No. 3,688 and has a heritage that includes the variety known commercially as 'Christmas Cheer' and the variety known as *Zygocactus truncatus* 'Parma'. It has a "reddish" colored bloom and a bloom life which provides a suitable shelf life at the retail level of sales. The variety also has a fast growth rate with substantial resistances to nutrient deficiencies and to fungus type diseases. The 'Kris Kringle' variety also has a substantial resistance to flower bud abscission and is endowed with a natural tendency to branch without inducement by pruning during the growth period before blooming. The growth rate, resistances, and branching tendencies are much sought after by growers of the so-called "Christmas Cactus" varieties.

The *Zygocactus truncatus* 'Lavender Doll' is yet another recent development among the so-called "Christmas Cactus" varieties and it forms the subject matter of U.S. Plant Pat. No. 3,690. The 'Lavender Doll' variety has a heritage that also includes the 'Christmas Cheer' variety and it has a growth habit which includes the mentioned resistance characteristics attributable to the 'Kris Kringle' variety but the natural tendency to branch without inducement by pruning during the growth period preceding blooming is not as profuse as that resident in the 'Kris Kringle' variety. The 'Lavender Doll' has what may be called a "purplish" colored bloom and like the 'Kris Kringle' variety, has rapidly acquired a broad market acceptance that has created a demand among nurserymen for different colored varieties of the so-called "Christmas Cactus" types and which have the growth rate and natural resistances to nutrient deficiencies, fungus type diseases and flower bud abscission that are exhibited by the 'Kris Kringle' and 'Lavender Doll' varieties.

A general objective of the invention has been to develop a variety of the *truncatus* species which has the growth rate and previously mentioned resistance characteristics that are associated with the 'Kris Kringle' and 'Lavender Doll' varieties but which have color characteristics that are distinguishable from those of such varieties and a bloom that matures at an earlier date than that of the 'Lavender Doll' variety.

The objectives of the invention have been fully realized by the development of the new plant variety described hereinafter in detail. The new plant variety was developed in a nursery located at Winter Garden, Fla., as a hybrid secured by cross-pollinating the flower of a plant specimen of a variety developed by the inventor from a vegetative mutation that appeared on a specimen of the 'Lavender Doll' variety with pollen from a plant specimen of the 'Kris Kringle' variety. The maternal variety is a research variety which has not appeared in the marketplace and it is distinguishable from the 'Lavender Doll' variety primarily by a growth habit which produces slightly larger phylloclades and specimens with somewhat poorer natural branching tendencies than those exhibited by the 'Lavender Doll' variety. The seeds taken from the fertilized seed pod of the maternal variety were cultivated at the mentioned nursery location and after prolonged observation of the seedlings, the hybridized plant of the new plant variety was selected and asexually reproduced by the inventor at the Winter Garden nursery through the propagation of stem cuttings taken from the original hybrid plant.

Through successive propagations, it has been ascertained that specimens of the new plant variety generally resemble the parent varieties but are distinguishable from the parent varieties and from other related varieties known to the inventor by a growth habit which is evident in specimens propagated and grown under nursery conditions utilized in the growing of tropical plants at Winter Garden, Fla., as combining the following principal characteristics:

1. A natural tendency to branch without inducement by pruning during the growth period before blooming and which is comparable to that of the 'Kris Kringle' variety.

2. A fast growth rate with resistances to nutrient deficiencies and fungus type diseases that are comparable to those of the 'Kris Kringle' and 'Lavender Doll' varieties.

3. A resistance to flower bud abscission that is comparable to those of the 'Kris Kringle' and 'Lavender Doll' varieties.

4. A flower which blooms from about one to three weeks earlier than that of the 'Lavender Doll' variety and has a bloom life of from about 6 to about 9 days and which has a pistil with a style that is translucent white at its proximal end and in color is dominated at its distal end by purplish red and/or reddish purple hues and with a stigma that is translucent white, and which also has tepals that have marginal blade areas which in color are dominated by purplish red and/or reddish purple hues and that include a sepaloid series of free tepals with inner whorl members having basal areas which in color are dominated by purplish pink hue, a perianth tube forming series of basally united tepals which form a translucent white vestigal carina at the throat of the tube, and a series of tube laminating tepals that usually number from 5 to 7 in the bloom.

The accompanying drawings serve, by color photographic means to illustrate the new plant variety and wherein:

One sheet is a color photograph of a blooming 6 month old plant specimen of the new plant variety, a second sheet shows color photographs of other blooming specimens and a third sheet embodies color photographs which further illustrate the blooms and certain parts thereof.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than one year of age from initial propagation and which were grown under 50–75% shaded glasshouse nursery conditions in the Winter Garden, Fla., area and wherein temperatures range from 60° to 85° F. during the winter months, from 75° to 95° F. during the summer months and are ambient during intervening periods.

DETAILED PLANT DESCRIPTION

Name: *Zygocactus truncatus* 'Christmas Charm'.

Parentage:

*Maternal.*—A research variety unavailable in the marketplace developed from a vegetative mutation that appeared on a plant specimen of the variety named *Zygocactus truncatus* 'Lavender Doll'.

*Paternal.*—*Zygocactus truncatus* 'Kris Kringle'.

Classification:

*Botanic* (*Britton and Rose, The Cactaceae, Constable and Co., Ltd., London* 1937, *Vol. IV*).—

| | |
|---|---|
| (1) Family: | *Cactaceae* |
| (2) Tribe: | *Cereeae* |
| (3) Sub-tribe | *Epiphyllanae* |
| (4) Genus: | *Zygocactus* |
| (5) Species: | *truncatus* (Haworth) Schumann |

*Commercial.*—Thanksgiving-Christmas blooming cactus.

Form: Terrestrial, shade-loving, succulent, leafless plant with jointed and branched stems.

Stems:

*General.*—Irregular with usually multi-chotomous branching of both upright and pendulous, adventitiously rootable, flattened phylloclades that have a prominent midrib and prominently toothed lateral wings.

*Phylloclades.*—General: Elongated and flat with transversely elongated, areole bearing, truncated apex, with inwardly tapering basal wing margins that merge through a broad usually pointed basal juncture with the phylloclade therebelow, and with an axillary areole associated with each tooth. Midrib: General — Extends longitudinally of phylloclade and continuously through joints with laterally tapering cortex at wing insertions. Pith surrounding vascular bundles that branch and provide lateral extension of the vascular system to marginal teeth. Texture — Smooth waxy epidermis with wax in small embedded scales and becoming corky in basal stem areas with age. Size (2–6 mos. old) — Length: Usually between 30 and 48 mm. with the average for respective plant specimens being usually between 37 and 47 mm. Thickness: Usually between 1.9 and 6.6 mm. with the average for respective plant specimens being usually between 2.6 and 4.0 mm. Color (at maturity) — Commonly dark yellowish green (near 10 GY 3/4), moderate yellow green (7.5 GY 6/4) (7.5 GY 5/6) (7.5 GY 5/4) (near 5 GY 6/6) (near 5 GY 6/4) (5 GY 5/4) and/or moderate olive green (7.5 GY 4/6) (7.5 GY 4/4) (7.5 GY 3/4) (5 GY 4/4). Wings: General shape — Generally flattened from midrib cortex to tooth insertions with slight thinning taper toward margins. Margins — Toothed (modified leaves). Texture — Succulent to leathery with smooth waxy epidermis having wax arranged in small embedded scales and becoming corky in basal plant areas with age. Size (2–6 mo. old) — Center thickness: Usually between 0.8 and 2.2 mm. Width (as measured from phylloclade axis to most offset lateral areole):

Usually between 6.7 and 18.1 mm. Color (at maturity) — Commonly moderate yellow green (7.5 GY 6/4) (7.5 GY 5/6) (7.5 GY 5/4) (5 GY 6/4) (5 GY 5/4) and/or moderate olive green (7.5 GY 4/6) (7.5 GY 4/4) (7.5 GY 3/4) (5 GY 4/4). Teeth: General — Generally flattened and tapered along margins from wing insertions to an apex having a hyaline, single cell, pointed spine with nonpredictable bending. Adaxial marginal shape: Usually concave. Abaxial marginal shape: Somewhat irregular but with generally an overall convex shape. Orientation — Usually projects distally of phylloclade base in an alternate arrangement. Margins — Entire with some tendencies toward undulation. Texture — Succulent to leathery with smooth waxy epidermis having wax in small embedded scales and becoming corky in basal plant areas with age. Number — Usually from 6 to 8 per phylloclade. Size (2–6 mos. old) — Center thickness: Usually between 0.4 and 1.5 mm. Areole to apex dimension (adaxial marginal side): Usually between 0.3 and 5.5 mm. for teeth located distally of basal teeth. Color (at maturity) — Commonly moderate yellow green (7.5 GY 6/4) (7.5 GY 5/6) (7.5 GY 5/4) (5 GY 6/4) (5 GY 5/4) and/or moderate olive green (7.5 GY 4/6) (7.5 GY 4/4) (7.5 GY 3/4) (5 GY 4/4). Areoles: Terminal areole — Large elongated oval-shaped with several acicular bristles, copious multi-cellular hairs, and several buds that may mature into either new phylloclades or flowers. The opposite end of the areole are located adjacent to subsidiary areoles which are in turn located at the axils of teeth that are located at the distal end of phylloclade. Axillary areoles — Acicular bristles without glochidia but having short, brownish to colorless, multicellular hairs. In areoles that are located below the teeth at the distal end of the phylloclade, there is usually only one bud that is frequently latent.

Buds: Unarmored, ovid and chlorophyllous when first immerging.

Flowers:

*General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series.*—General: Free tepals inserted on top of ovary. Shape: Deltoid in outer members of the whorl and with the inner members being irregular in shape and varying with a predominance of elliptic, lanceolate and oblanceolate shapes and with tips which vary from acute to acuminate. Margins are entire with sparse irregular teeth appearing mainly in apex areas of the inner members of the whorl. Texture: Succulent and glabrous outer whorl members and grading inwardly in the whorl to silken blades with fleshy basal areas. Number: Usually 9 or 10. Size (at full bloom): Base-tip dimension — Usually less than 30 mm. Maximum width dimension — Usually less than 15 mm. Color: Outer whorl members — Varies with the smallest outer whorl members having a continuous field that in color has a yellow green hue and with the larger outer whorl members having tendencies toward the color characteristics of the inner whorl members. Commonly strong yellow green (5 GY 7/8) (5 GY 6/8) (2.5 GY 7/8) (2.5 GY 6/8) and/or moderate yellow green (5 GY 7/6) (near 5 GY 6/6) (2.5 GY 7/6) (2.5 GY 6/6) (2.5 GY 5/6) for smallest members. Inner whorl members — Marginal areas have a color dominated by reddish purple and/or purplish red hues and basal areas have a color which is dominated by a purplish pink hue and which merges distally with the marginal colorations. Commonly pale purplish pink (5 RP 9/2) (5 RP 8/4) (7.5 RP 8/4), light purplish pink (5 RP 8/6), moderate purplish pink (5 RP 7/8) (5 RP 7/6) (2.5 RP 7/6) and/or dark purplish pink (5 RP 6/8) in the basal areas and commonly moderate purplish red (near 5 RP 4/8), strong reddish purple (10 P 5/10) (10 P 4/10) (2.5 RP 5/10) (2.5 RP 4/10) and/or moderate reddish purple (near 10 P 5/8) (2.5 RP 5/8) (near 2.5 RP 4/8) in the marginal areas. Orientation at full bloom: Generally acute to slightly reflexed.

*Tube laminating series.*—General: Tepals inserted on ovary and basally united below the throat as outer laminations on the perianth tube and with progressively greater amounts of basal fusion inwardly in the whorl. Shape: Grading inwardly in whorl with progressively longer base-tip dimensions and with spatulate to oblanceolate tepals and with free portion of the blade being generally lanceolate to oblanceolate and with a broad acute tip. Entire margins with sparse irregular teeth mainly in apex areas. Texture: Succulent, slightly fleshy, basal areas with silken blades. Number: Usually from 5 to 7. Size (at full bloom): Base-tip dimension — usually between 32 and 58 mm. Maximum width dimensions — Usually between 11 and 17 mm. Color: Tepals with translucent white basal areas that extend distally in the tepals and merge with marginal blade areas that in color are dominated by a reddish purple hue. Commonly strong reddish purple (10 P 5/10) (2.5 RP 4/10) and/or moderate reddish purple (near 2.5 RP 4/8) in marginal areas. Orientation at full bloom: Generally acute to reflexed.

*Tube forming series.*—General: Tepals basally united to form hollow perianth tube that is inserted on ovary and equipped with a vestigal carina at throat. Shape: Perianth tube — Elongated and ellipsoidal in cross section. Blades — Irregular and elliptic to lanceolate with acute tips. Entire margins with sparse, irregular teeth mainly in apex areas. Carina (keel) — Vestigal and superficially transcending. Texture: Perianth tube — Thick, succulent and slightly ribbed. Blades — Translucent and silken. Carina (keel) — Fleshy. Blade number: Usually 8. Size (at full bloom): Perianth tube — Base to keel length. Usually between 30 and 33 mm. along axis of tube with average length differences between measurements along dorsal and ventral sides for respective specimens usually being between 2.5 and 5.5 mm. Internal major axis (at throat): Usually between 8 and 12 mm. when measured perpendicular to axis of perianth tube. Internal minor axis (at throat): Usually between 6 and 9 mm. when measured perpendicular to axis of perianth tube. Blades — Length (keel to tip): Usually between 26 and 34 mm. Width (maximum): Usually between 12 and 19 mm. Color (at full bloom): Perianth tube — Commonly translucent white. Blades — Tepal blades with maginal blade areas which in color are dominated by purplish red and/or reddish purple hues that merge with a translucent white basal blade area that extends distally of the throat. Commonly dark purplish red (near 5 RP 3/8), strong reddish purple (2.5 RP 4/10) (10 P 5/10) and/or deep reddish purple (2.5 RP 3/10) (near 2.5 RP 3/8) in marginal areas. Carina (keel) — Translucent white. Orientation at full bloom: Acute to reflexed.

*Androecium* (*stamens*).—General: Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. Stamen number: Tube attached group — Usually between 90 and 95. Basally united group — Usually between 16 and 22. Filament: General — Translucent and glabrous with anther connective. Shape — Long, slender and gradually tapering from base to anther connective. Texture — Glabrous and silken. Color — A translucent white. Size (at full bloom) — Length: Tube attached group — Usually between 39 and 49 mm. Basally united group — Usually between 35 and 49 mm. Diameter: Usually between 0.2 and 0.3 mm. intermediate the opposite ends. Anthers: General — Adnate with four longitudinally dehiscent pollen sacs. Shape — Elongated. Texture — Waxy. Color (post dehiscence i.e. pollen color) — Usually light greenish yellow (7.5 Y 9/6) and/or pale greenish yellow (7.5 Y 9/4) (10 Y 9/4).

*Gynoecium* (*pistil*).—General: Compound, parietal placentation with united style surrounded by annular diffuse nectary at its insertion. Style: General — Stout and inserted in ovary. Shape — Elongated, cylindrical and generally tapering. Texture — Fleshy and glabrous with short inner glutinous hairs at distal end. Color — A translucent white proximal end area and a distal end that in color is dominated by purplish red and/or reddish purple hues. Commonly dark purplish red (near 5 RP 3/8), strong reddish purple (2.5 RP 4/10) and/or deep reddish purple (2.5 RP 3/10) (near 2.5 RP 3/8) at the distal end. Size (at full bloom) — Length: Usually about 60 mm. Diameter: Usually between 0.7 and 0.9 mm. intermediate the opposite ends. Stigma: General — Exserted and erect with usually 6 or 7 inner marginally adhering lobes. Shape — Elongated and tapering toward lobe tips and having relatively blunt apices. Texture — Fleshy and smooth with short glutinous hairs. Color — A translucent white. Size (lobe length at full bloom) — Usually between 2.7 and 4.3 mm. Ovary: General — Epigynous with thin epidermis and distally located concavity and with single cavity having 6 or 7 carpels with numerous ovules. Shape — Terete to ovoid and generally broadening from insertion to floral end. Texture — Succulent and glabrous with thin outer epidermis. Color — Commonly strong yellow green (5 GY 7/8) (5 GY 6/8) (2.5 GY 7/8) (2.5 GY 6/8) and/or moderate yellow green (5 GY 7/6) (near 2.5 GY 7/6) (near 5 GY 6/6) (2.5 GY 6/6) (2.5 GY 5/6). Size (at full bloom) — Length (insertion to concavity base): Commonly about 11 mm. Major axis (distal end of concavity): Usually between 7.5 and 10 mm. Minor axis (distal end of concavity): Usually between 6 and 8 mm.

Growing characteristics: A fast growth rate comparable to the 'Kris Kringle' and 'Lavender Doll' varieties, with an upright and compact (dense) appearance as evidenced by erect stems with heavy (frequent) branching that tends to occur naturally without inducement by pruning. A resistance to nutrient deficiencies and fungus type diseases that is comparable to those of the 'Kris Kringle' and 'Lavender Doll' varieties and a resistance to flower bud abscission that is similarly comparable to such varieties. A bloom life (from initial tepal separation to initial tepal withering) of from about 6 to about 9 days.

The following is a general description of a specimen of the new plant variety that was grown from the propagation of a single phylloclade in a nursery at Winter Garden, Fla.

Age of plant: 6 months from initial propagation.
Branches from propagated cutting: 3
Total number of phylloclades grown from cutting: 19.
General:

| Branch No. | No. of Phylloclades | Max. Length | No. of Tips |
|---|---|---|---|
| 1 | 10 | 156 mm. | 4 |
| 2 | 6 | 140 mm. | 3 |
| 3 | 3 | 81 mm. | 2 |

Midribs:

| Branch No. | Length (avg.) | Thickness (avg.) |
|---|---|---|
| 1 | 40 mm. | 3.9 mm. |
| 2 | 45 mm. | 3.8 mm. |
| 3 | 39 mm. | 3.8 mm. |

Wings:

| Branch No. | Center Thickness (avg.) | Max. Width (avg.) |
|---|---|---|
| 1 | 1.6 mm. | 11.5 mm. |
| 2 | 1.7 mm. | 11.7 mm. |
| 3 | 1.2 mm. | 9.7 mm. |

Teeth:

| Branch No. | No./Phylloclades (avg.) | Center Thickness (avg.) | Areole to Apex Dimension (avg.) |
|---|---|---|---|
| 1 | 7.5 | 0.9 mm. | 2.5 mm. |
| 2 | 8.3 | 0.9 mm. | 3.5 mm. |
| 3 | 6.7 | 0.6 mm. | 1.2 mm. |

Phylloclade color: Moderate yellow green (7.5 GY 5/4) (7.5 GY 5/6).

The following is a general description of a flower of the new plant variety which bloomed in December on a plant grown under shaded glasshouse nursery conditions in Winter Garden, Fla.

Bloom life: 8 days.

Sepaloid series of tepals:

*Number.*—10.

*Size (at full bloom).*—Maximum base-tip dimension: 29 mm. Minimum base-tip dimension: 3 mm. Maximum width dimension: 12 mm.

*Color.*—Most outer whorl members strong yellow green (5 GY 6/8) (2.5 GY 7/8) and/or moderate yellow green (5 GY 7/6). Pale purplish pink (5 RP 9/2) in basal area of inner whorl members and strong reddish purple (10 P 5/10) (2.5 RP 5/10) (2.5 RP 4/10) in marginal areas of inner whorl members.

Tube laminating series:

*Number.*—7.

*Size (at full bloom).*—Maximum base-tip dimension: 52 mm. Minimum base-tip dimension: 23 mm. Maximum width dimension: 14 mm. Minimum width dimension: 10 mm.

*Color.*—Translucent white basal area. Strong reddish purple (10 P 5/10) and moderate reddish purple (2.5 RP 4/8) in marginal areas.

Tube forming series of tepals:

*Number.*—8.

*Size (at full bloom).*—Perianth tube: Base to throat length — 32 mm. Interior major axis (at throat) — 9 mm. Interior minor axis (at throat) — 7 mm. Blades: Maximum length (throat to tip) — 33 mm. Minimum length (throat to tip) — 27 mm. Maximum width — 16 mm. Minimum width — 13 mm.

*Color.*—Perianth tube: A translucent white. Blades: Translucent white basal area and strong reddish purple (2.5 RP 4/10) and/or deep reddish purple (2.5 RP 3/10) in marginal and distal blade areas. Carina (keel): Translucent white.

Androecium:

*Stamen number.*—Tube attached group: 93. Basally united group: 17.

*Filaments.*—Color: A translucent white. Size (at full bloom): Length — Tube attached group: 43.5 mm. (avg.). Basally united group: 45 mm. (avg.). Diameter — 0.25 mm. (avg.).

*Anthers.*—Color (post dehiscense): Pale greenish yellow (7.5 Y 9/4).

Gynoecium (pistil):

*Style.*—Color: Translucent white proximal area. Deep reddish purple (2.5 RP 3/10) and strong reddish purple (2.5 RP 4/10) in distal area. Size (at full bloom): Length — 60 mm. Diameter — 0.85 mm. intermediate the opposite ends.

*Stigma.*— Color: A translucent white. Size (lobe length): About 3.5 mm. (avg.).

*Ovary.*—Color: Moderate yellow green (5 GY 7/6) (2.5 GY 7/6) (2.5 GY 6/6). Size (at full bloom): Length (insertion to concavity base) — 11 mm. Major axis (distal end of concavity) — 9 mm. Minor axis (distal end of concavity) — 7.3 mm.

We claim:

1. The new and distinct hybrid plant variety of the Cactaceae family as described and illustrated and which is principally distinguished by a growth habit that combines the following characteristics:

1. A natural tendency to branch during the growth period without the need for inducement by pruning,
2. A fast growth rate which is comparable to the growth rates exhibited by specimens of the 'Kris Kringle' and 'Lavender Doll' varieties,
3. Resistances to nutrient deficiencies, to fungus type diseases, and to flower bud abscission that are comparable to those exhibited by specimens of the 'Kris Kringle' and 'Lavender Doll' varieties, and
4. A flower having a bloom life of from about 6 to about 9 days, a pistil with a style that is translucent white at its proximal end, and at its distal end is in color dominated by purplish red and/or reddish purple hues and with a stigma which is translucent white, and tepals which have marginal blade areas that in color are dominated by purplish red and/or reddish purple hues and which include a sepaloid series of free tepals with inner whorl members having basal areas that in color are dominated by a purplish pink hue, a perianth tube forming series of basally united tepals that form a translucent white vestigal carina at the throat of the tube, and a series of tube laminating tepals which usually number from 5 to 7 in the bloom.

* * * * *

UNITED STATES PATENT AND TRADEMARK OFFICE

CERTIFICATE OF CORRECTION

PATENT NO. : P.P. 4196

DATED : January 24, 1978

INVENTOR(S) : Barnell L. Cobia and Stephen H. Griffith

It is certified that error appears in the above-identified patent and that said Letters Patent are hereby corrected as shown below:

Col. 4, Line 7, before "Maternal" insert -- A. --; Line 12, before "Paternal" insert -- B. --; Line 14, before "Botanic" insert -- A. --; Line 23, before "Commercial" insert -- B. --; Line 28, before "General" insert -- A. --; Line 33, before "Phylloclades" insert -- B. --; Line 33, before "General" insert -- [1] --; Line 39, before "Midrib" insert -- [2] --; Line 39, before "General" insert -- (a) --; Line 44, before "Texture" insert -- (b) --; Line 47, before "Size" insert -- (c) --; Line 47, before "Length" insert -- (1) --; Line 50, before "Thickness" insert -- (2) --; Line 53, before "Color" insert -- (d) --; Line 59, before "Wings" insert -- [3] --; Line 59, before "General shape" insert -- (a) --; Line 61, before "Margins" insert -- (b) --; Line 62, before "Texture" insert -- (c) --; Line 65, before "Size" insert -- (d) --; Line 66, before "Center thickness" insert -- (1) --; Line 67, before "Width" insert -- (2) --; Col. 5, Line 1, before "Color" insert -- (e) --; Line 6, before "Teeth" insert -- [4] --; Line 6, before "General" insert -- (a) --; Line 9, before "Adaxial" insert -- (1) --; Line 10, before "Abaxial" insert -- (2) --; Line 12, before "Orientation" insert -- (b) --; Line 14, before "Margins" insert -- (c) --; Line 15, before "Texture" insert -- (a) --; Line 18, before "Number" insert -- (e) --; Line 19, before "Size" insert -- (f) --; Line 21, before "Center thickness" insert -- (1) --; Line 22, before "Areole" insert -- (2) --; Line 24, before "Color" insert -- (g) --; Line 28, before "Areoles" insert -- [5] --; Line 28, before "Terminal" insert -- (a) --; Line 35, before "Axil-" insert -- (b) --; Line 45, before "General" insert -- A. --; Line 52, before "Sepaloid" insert -- B. --; Line 52, before "General" insert -- [1] --; Line 53, before "Shape" insert -- [2] --; Line 60, before "Texture" insert -- [3] --; Line 63, before "Number" insert -- [4] --; Line 63, before "Size" insert -- [5] --; Line 64, before "Base-" insert -- (a) --; Line 65, before "Maximum" insert -- (b) --; Line 66, before "Color" insert -- [6] --; Line 66, before "Outer" insert -- (a) --; Col. 6, Line 8, before "Inner" insert -- (b) --; Line 22, before "Orienta-" insert -- [7] --; Line 25, before "Tube"

UNITED STATES PATENT AND TRADEMARK OFFICE

CERTIFICATE OF CORRECTION

PATENT NO. : P.P. 4196

DATED : January 24, 1978

INVENTOR(S) : Barnell L. Cobia and Stephen H. Griffith

It is certified that error appears in the above-identified patent and that said Letters Patent are hereby corrected as shown below:

insert -- C. --; Line 25, before "General" insert -- [1] --; Line 29, before "Shape" insert -- [2] --; Line 35, before "Texture" insert -- [3] --; Line 37, before "Number" insert -- [4] --; Line 37, before "Size" insert -- [5] --; Line 38, before "Base-" insert -- (a) --; Line 39, before "Maximum" insert -- (b) --; Line 40, before "Color" insert -- [6] --; Line 47, before "Orientation" insert -- [7] --; Line 49, before "Tube" insert -- D. --; Line 49, before "General" insert -- [1] --; Line 52, before "Shape" insert -- [2] --; Line 52, before "Perianth" insert -- (a) --; Line 53, before "Blades" insert -- (b) --; Line 56, before "Carina" insert -- (c) --; Line 57, before "Texture" insert -- [3] --; Line 57, before "Perianth" insert -- (a) --; Line 59, before "Blades" insert -- (b) --; Line 59, before "Carina" insert -- (c) --; Line 60, before "Blade" insert -- [4] --; Line 60, before "Size" insert -- [5] --; Line 61, before "Perianth" insert -- (a) --; Line 61, before "Base" insert -- (1) --; Line 66, before "Internal" insert -- (2) --; Line 68, before "Internal" insert -- (3) --; Col. 7, Line 3, before "Blades" insert -- (b) --; Line 3, before "Length" insert -- (1) --; Line 4, before "Width" insert -- (2) --; Line 5, before "Color" insert -- [6] --; Line 6, before "Perianth" insert -- (a) --; Line 7, before "Blades" insert -- (b) --; Line 15, before "Carina" insert -- (c) --; Line 16, before "Orientation" insert -- [7] --; Line 18, before "Androecium" insert -- E. --; Line 18, before "General" insert -- [1] --; Line 25, before "Stamen" insert -- [2] --; Line 26, before "Tube" insert -- (a) --; Line 27, before "Basally" insert -- (b) --; Line 28, before "Filament" insert -- [3] --; Line 28, before "General" insert -- (a) --; Line 29, before "Shape" insert -- (b) --; Line 31, before "Texture" insert -- (c) --; Line 32, before "Color" insert -- (d) --; Line 32, before "Size" insert -- (e) --; Line 33, before "Length" insert -- (1) --; Line 33, before "Tube" insert -- (a) --; Line 34, before "Basally" insert -- (b) --; Line 35, before "Diameter" insert -- (2) --; Line 37, before "Anthers" insert -- [7] --;

UNITED STATES PATENT AND TRADEMARK OFFICE

CERTIFICATE OF CORRECTION

PATENT NO. : P.P. 4196

DATED : January 24,1978

INVENTOR(S) : Barnell L. Cobia and Stephen H. Griffith

It is certified that error appears in the above-identified patent and that said Letters Patent are hereby corrected as shown below:

Line 37, before "General" insert -- (a) --; Line 39, before "Shape" insert -- (b) --; Line 39, before "Texture" insert -- (c) --; Line 39, before "Color" insert -- (d) --; Line 43, before "Gynoecium" insert -- F. --; Line 43, before "General" insert -- [1] --; Line 45, before "Style" insert -- [2] --; Line 46, before "General" insert -- (a) --; Line 46, before "Shape" insert -- (b) --; Line 48, before "Texture" insert -- (c) --; Line 49, before "Color" insert -- (d) --; Line 55, before "Size" insert -- (e) --; Line 56, before "Length" insert -- (1) --; Line 57, before "Diameter" insert -- (2) --; Line 58, before "Stigma" insert -- [3] --; Line 58, before "General" insert -- (a) --; Line 60, before "Shape" insert -- (b) --; Line 62, before "Texture" insert -- (c) --; Line 63, before "Color" insert -- (d) --; Line 64, before "Size" insert -- (e) --; Line 66, before "Ovary" insert -- [4] --; Line 66, before "General" insert -- (a) --; Col. 8, Line 1, before "Shape" insert -- (b) --; Line 2, before "Texture" insert -- (c) --; Line 4, before "Color" insert -- (d) --; Line 8, before "Size" insert -- (e) --; Line 8, before "Length" insert -- (1) --; Line 10, before "Major" insert -- (2) --; Line 11, before "Minor" insert -- (3) --; Line 48, under "Thickness (avg.)" delete "3.8" (last occurrence" and substitute -- 2.8 --; Col. 9, Line 7, before "Number" insert -- (1) --; Line 8, before "Size" insert -- (2) --; Line 8, before "Maximum" insert -- (a) --; Line 9, before "Minimum" insert -- (b) --; Line 10, before "Maximum" insert -- (c) --; Line 11, before "Color" insert -- (3) --; Line 19, before "Number" insert -- (1) --; Line 20, before "Size" insert -- (2) --; Line 20, before "Maximum" insert -- (a) --; Line 21, before "Minimum" insert -- (b) --; Line 22, before "Maximum" insert -- (c) --; Line 22, before "Minimum" insert -- (d) --; Line 24, before "Color" insert -- (3) --; Line 28, before "Number" insert -- (1) --; Line 29, before "Size" insert -- (2) --; Line 29, before "Perianth" insert -- (a) --; Line 29, before "Base" insert -- (1) --; Line 30, before "Interior" insert -- (2) --; Line 31, before "Interior" insert -- (3) --; Line 32, before "Blades" insert

UNITED STATES PATENT AND TRADEMARK OFFICE

CERTIFICATE OF CORRECTION

PATENT NO. : P.P. 4196

DATED : January 24, 1978

INVENTOR(S) : Barnell L. Cobia and Stephen H. Griffith

It is certified that error appears in the above-identified patent and that said Letters Patent are hereby corrected as shown below:

-- (b) --; Line 32, before "Maximum" insert -- (1) --; Line 33, before "Minimum" insert -- (2) --; Line 34, before "Maximum" insert -- (3) --; Line 34, before "Minimum" insert -- (4) --; Line 36, before "Color" insert -- (3) --; Line 36, before "Perianth" insert -- (a) --; Line 36, before "Blades" insert -- (b) --; Line 40, before "Carina" insert -- (c) --; Line 42, before "Stamen" insert -- (1) --; Line 42, before "Tube" insert -- (a) --; Line 42, before "Basally" insert -- (b) --; Line 44, before "Filaments" insert -- (2) --; Line 44, before "Color" insert -- (a) --; Line 44, before "Size" insert -- (b) --; Line 45, before "Length" insert -- (1) --; Line 45, before "Tube" insert -- (a) --; Line 46, before "Basally" insert -- (b) --; Line 47, before "Diameter" insert -- (2) --; Col. 10, Line 1, before "Anthers" insert -- (3) --; Line 1, before "Color" insert -- (a) --; Line 4, before "Style" insert -- (1) --; Line 4, before "Color" insert -- (a) --; Line 6, before "Size" insert -- (b) --; Line 7, before "Length" insert -- (1) --; Line 7, before "Diameter" insert -- (2) --; Line 9, before "Stigma" insert -- (2) --; Line 9, before "Color" insert -- (a) --; Line 9, before "Size" insert -- (b) --; Line 11, before "Ovary" insert -- (3) --; Line 11, before "Color" insert -- (a) --; Line 12, before "Size" insert -- (b) --; Line 13, before "Length" insert -- (1) --;; Line 14, before "Major" insert -- (2) --; Line 15, before "Minor" insert -- (3) --;

Signed and Sealed this

*Twenty-third* Day of *October 1979*

[SEAL]

*Attest:*

RUTH C. MASON
*Attesting Officer*

LUTRELLE F. PARKER
*Acting Commissioner of Patents and Trademarks*